(12) United States Patent
Marga et al.

(10) Patent No.: US 9,752,122 B2
(45) Date of Patent: Sep. 5, 2017

(54) EDIBLE AND ANIMAL-PRODUCT-FREE MICROCARRIERS FOR ENGINEERED MEAT

(71) Applicant: Modern Meadow, Inc., Brooklyn, NY (US)

(72) Inventors: Francoise Suzanne Marga, Columbia, MO (US); Brendan Patrick Purcell, Brooklyn, NY (US); Gabor Forgacs, Potsdam, NY (US); Andras Forgacs, Palo Alto, CA (US)

(73) Assignee: Modern Meadow, Inc., Brooklyn, NY (US)

( * ) Notice: Subject to any disclaimer, the term of this patent is extended or adjusted under 35 U.S.C. 154(b) by 182 days.

(21) Appl. No.: 14/486,850

(22) Filed: Sep. 15, 2014

(65) Prior Publication Data

US 2015/0079238 A1    Mar. 19, 2015

Related U.S. Application Data

(60) Provisional application No. 61/877,865, filed on Sep. 13, 2013.

(51) Int. Cl.
*C12N 5/077* (2010.01)
*A23P 10/20* (2016.01)
*A23L 13/00* (2016.01)

(52) U.S. Cl.
CPC ............ *C12N 5/0658* (2013.01); *A23L 13/00* (2016.08); *A23P 10/20* (2016.08); *A23V 2002/00* (2013.01);
(Continued)

(58) Field of Classification Search
None
See application file for complete search history.

(56) References Cited

U.S. PATENT DOCUMENTS 3,497,363 A    2/1970    Fox
3,512,993 A    5/1970    Conley et al.
(Continued)

FOREIGN PATENT DOCUMENTS

CA    2306346 A1    1/1999
EP    1589098 A1    10/2005
(Continued)

OTHER PUBLICATIONS

Munarin et al., "Pectin-Based Injectable Biomaterials for Bone Tissue Engineering"—Biomacromolecules, 12(3), 2011, pp. 568-577.*

(Continued)

*Primary Examiner* — Elizabeth Gwartney
(74) *Attorney, Agent, or Firm* — Oblon, McClelland, Maier & Neustadt, L.L.P.

(57) ABSTRACT

Edible microcarriers, including microcarrier beads, microspheres and microsponges, appropriate for use in a bioreactor to culture cells that may be used to form a comestible engineered meat product. For example, the edible microcarriers described herein may include porous microcarriers that may be used to grow cells (e.g., smooth muscle cells) and may be included with the cells in the final engineered meat product, without requiring modification or removal of the cells from the microcarriers. In a particular example, the edible microcarriers may be formed of cross-linked pectin, such as pectin-thiopropionylamide (PTP), and RGD-containing polypeptide, such as thiolated cardosin A. Methods of forming edible microcarriers, methods of using the edible microcarriers to make engineered meat, and engineered meat including the edible microcarriers are also described herein.

15 Claims, 6 Drawing Sheets

(52) U.S. Cl.
CPC ...... *C12N 2500/92* (2013.01); *C12N 2531/00* (2013.01)

(56) References Cited

U.S. PATENT DOCUMENTS

| | | | |
|---|---|---|---|
| 3,956,560 A | 5/1976 | Smith, II | |
| 4,089,333 A | 5/1978 | Utsuo et al. | |
| 4,247,279 A | 1/1981 | Masters | |
| 4,291,992 A | 9/1981 | Barr et al. | |
| 4,294,241 A | 10/1981 | Miyata | |
| 4,404,033 A | 9/1983 | Steffan | |
| 4,465,472 A | 8/1984 | Urbaniak | |
| 4,564,597 A | 1/1986 | Lerner et al. | |
| 4,585,139 A | 4/1986 | Bronson et al. | |
| 4,646,106 A | 2/1987 | Howkins | |
| 4,665,492 A | 5/1987 | Masters | |
| 4,673,304 A | 6/1987 | Liu et al. | |
| 4,772,141 A | 9/1988 | Sanders, Jr. et al. | |
| 4,889,438 A | 12/1989 | Forsyth et al. | |
| 4,896,980 A | 1/1990 | Sanders, Jr. et al. | |
| 4,921,365 A | 5/1990 | Sanders, Jr. et al. | |
| 4,948,280 A | 8/1990 | Sanders, Jr. et al. | |
| 4,969,758 A | 11/1990 | Sanders, Jr. et al. | |
| 4,980,112 A | 12/1990 | Masters | |
| 4,980,403 A | 12/1990 | Bateman et al. | |
| 5,016,121 A | 5/1991 | Peddle et al. | |
| 5,039,297 A | 8/1991 | Masters | |
| 5,040,911 A | 8/1991 | Sanders, Jr. et al. | |
| 5,134,569 A | 7/1992 | Masters | |
| 5,171,273 A | 12/1992 | Silver et al. | |
| 5,204,055 A | 4/1993 | Sachs et al. | |
| 5,216,606 A | 6/1993 | Lentz et al. | |
| 5,490,962 A | 2/1996 | Cima et al. | |
| 5,492,937 A | 2/1996 | Bogentoft et al. | |
| 5,546,313 A | 8/1996 | Masters | |
| 5,599,695 A | 2/1997 | Pease et al. | |
| 5,605,662 A | 2/1997 | Heller et al. | |
| 5,658,802 A | 8/1997 | Hayes et al. | |
| 5,697,324 A | 12/1997 | van der Lely | |
| 5,702,717 A | 12/1997 | Cha et al. | |
| 5,739,832 A | 4/1998 | Heinzl et al. | |
| 5,797,898 A | 8/1998 | Santini, Jr. et al. | |
| 5,798,779 A | 8/1998 | Nakayasu et al. | |
| 5,831,070 A | 11/1998 | Pease et al. | |
| 5,929,208 A | 7/1999 | Heller et al. | |
| 6,087,102 A | 7/2000 | Chenchik et al. | |
| 6,103,528 A | 8/2000 | An et al. | |
| 6,109,717 A | 8/2000 | Kane et al. | |
| 6,123,861 A | 9/2000 | Santini, Jr. et al. | |
| 6,132,468 A | 10/2000 | Mansmann | |
| 6,139,831 A | 10/2000 | Shivashankar et al. | |
| 6,171,797 B1 | 1/2001 | Perbost | |
| 6,197,575 B1 | 3/2001 | Griffith et al. | |
| 6,239,273 B1 | 5/2001 | Pease et al. | |
| 6,261,493 B1 | 7/2001 | Gaylo et al. | |
| 6,336,480 B2 | 1/2002 | Gaylo et al. | |
| 6,383,549 B1 | 5/2002 | Agostinelli | |
| 6,387,707 B1 | 5/2002 | Seul et al. | |
| 6,394,585 B1 | 5/2002 | Ross | |
| 6,402,403 B1 | 6/2002 | Speakman | |
| 6,419,883 B1 | 7/2002 | Blanchard | |
| 6,451,346 B1 | 9/2002 | Shah et al. | |
| 6,454,811 B1 | 9/2002 | Sherwood et al. | |
| 6,455,311 B1 | 9/2002 | Vacanti | |
| 6,495,102 B1 | 12/2002 | Suslick et al. | |
| 6,497,510 B1 | 12/2002 | Delametter et al. | |
| 6,514,518 B2 | 2/2003 | Monkhouse et al. | |
| 6,527,378 B2 | 3/2003 | Rausch et al. | |
| 6,536,873 B1 | 3/2003 | Lee et al. | |
| 6,536,895 B2 | 3/2003 | Kashiwagi et al. | |
| 6,538,089 B1 | 3/2003 | Samra et al. | |
| 6,543,872 B2 | 4/2003 | Ohtsuka et al. | |
| 6,547,994 B1 | 4/2003 | Monkhouse et al. | |
| 6,548,263 B1 | 4/2003 | Kapur et al. | |
| 6,550,904 B2 | 4/2003 | Koitabashi et al. | |
| 6,561,626 B1 | 5/2003 | Min et al. | |
| 6,561,642 B2 | 5/2003 | Gonzalez | |
| 6,565,176 B2 | 5/2003 | Anderson et al. | |
| 6,835,390 B1 | 12/2004 | Vein | |
| 6,942,830 B2 | 9/2005 | Mülhaupt et al. | |
| 6,979,670 B1 | 12/2005 | Lyngstadaas et al. | |
| 7,051,654 B2 | 5/2006 | Boland et al. | |
| 7,166,464 B2 | 1/2007 | McAllister et al. | |
| 7,270,829 B2 | 9/2007 | Van Eelen | |
| 7,625,198 B2 | 12/2009 | Lipson et al. | |
| 8,076,137 B2 | 12/2011 | McAllister et al. | |
| 8,703,216 B2 | 4/2014 | Forgacs et al. | |
| 2002/0031500 A1 | 3/2002 | MacLaughlin et al. | |
| 2002/0059049 A1 | 5/2002 | Bradbury et al. | |
| 2002/0064808 A1 | 5/2002 | Mutz et al. | |
| 2002/0064809 A1 | 5/2002 | Mutz et al. | |
| 2002/0084290 A1 | 7/2002 | Materna | |
| 2002/0089561 A1 | 7/2002 | Weitzel et al. | |
| 2002/0090720 A1 | 7/2002 | Mutz et al. | |
| 2002/0106412 A1 | 8/2002 | Rowe et al. | |
| 2002/0160109 A1 | 10/2002 | Yeo et al. | |
| 2002/0164319 A1 | 11/2002 | Khaw et al. | |
| 2002/0173586 A1 | 11/2002 | Jeong et al. | |
| 2002/0182633 A1 | 12/2002 | Chen et al. | |
| 2002/0188349 A1 | 12/2002 | McAllister et al. | |
| 2003/0012805 A1 | 1/2003 | Chen et al. | |
| 2003/0031500 A1 | 2/2003 | Bouveresse | |
| 2003/0032203 A1 | 2/2003 | Sabatini et al. | |
| 2003/0059537 A1 | 3/2003 | Chilkoti et al. | |
| 2003/0100824 A1 | 5/2003 | Warren et al. | |
| 2003/0113433 A1 | 6/2003 | Tempesta | |
| 2003/0153078 A1 | 8/2003 | Libera et al. | |
| 2003/0175410 A1 | 9/2003 | Campbell et al. | |
| 2003/0190438 A1 | 10/2003 | Suzuki et al. | |
| 2004/0039727 A1 | 2/2004 | Dessloch et al. | |
| 2004/0219133 A1 | 11/2004 | Lyles | |
| 2005/0118326 A1 | 6/2005 | Anfinsen et al. | |
| 2005/0163912 A1 | 7/2005 | White | |
| 2005/0276791 A1 | 12/2005 | Hansford et al. | |
| 2006/0121006 A1 | 6/2006 | Chancellor et al. | |
| 2007/0142916 A1 | 6/2007 | Olson et al. | |
| 2007/0231787 A1 | 10/2007 | Voelker | |
| 2007/0238167 A1 | 10/2007 | Perez et al. | |
| 2008/0070304 A1 | 3/2008 | Forgacs et al. | |
| 2008/0171994 A1 | 7/2008 | Williams et al. | |
| 2009/0069893 A1 | 3/2009 | Paukshto et al. | |
| 2009/0142307 A1 | 6/2009 | Athanasiou et al. | |
| 2009/0208466 A1 | 8/2009 | Yoo et al. | |
| 2009/0209823 A1 | 8/2009 | Yamane | |
| 2009/0248145 A1 | 10/2009 | Chan et al. | |
| 2010/0041134 A1 | 2/2010 | Forgacs et al. | |
| 2010/0189712 A1 | 7/2010 | L'Heureux et al. | |
| 2011/0165301 A1 | 7/2011 | Blumenthal | |
| 2011/0212179 A1 | 9/2011 | Liu | |
| 2011/0212501 A1 | 9/2011 | Yoo | |
| 2011/0250308 A1 | 10/2011 | Jun et al. | |
| 2012/0023777 A1 | 2/2012 | Greene | |
| 2012/0116568 A1 | 5/2012 | Murphy et al. | |
| 2012/0190473 A1 | 7/2012 | Swist | |
| 2012/0230950 A1 | 9/2012 | Niklason et al. | |
| 2013/0029008 A1 | 1/2013 | Forgacs et al. | |
| 2013/0142763 A1 | 6/2013 | Carlson et al. | |
| 2013/0255003 A1 | 10/2013 | Forgacs et al. | |
| 2013/0287896 A1 | 10/2013 | Harel et al. | |
| 2014/0017284 A1 | 1/2014 | Yang et al. | |
| 2014/0093618 A1 | 4/2014 | Forgacs et al. | |
| 2014/0205729 A1 | 7/2014 | Didzbalis et al. | |
| 2016/0097109 A1 | 4/2016 | Forgacs et al. | |
| 2016/0227831 A1 | 8/2016 | Marga | |
| 2016/0348078 A1 | 12/2016 | Forgacs et al. | |

FOREIGN PATENT DOCUMENTS

| | | |
|---|---|---|
| EP | 2090584 A1 | 8/2009 |
| JP | 06017378 A | 1/1994 |
| JP | 09-047502 A | 2/1997 |
| KR | 100716015 | 5/2007 |
| WO | WO99/31222 A1 | 6/1999 |
| WO | WO99/31223 A1 | 6/1999 |

(56) References Cited

FOREIGN PATENT DOCUMENTS

| WO | WO01/68811 A2 | 9/2001 |
|---|---|---|
| WO | WO2005/081970 A2 | 9/2005 |
| WO | WO2006/132504 A | 12/2006 |
| WO | WO2007/124023 A2 | 11/2007 |
| WO | WO2009/070720 A1 | 6/2009 |
| WO | WO2010/008905 A2 | 1/2010 |
| WO | WO2011051983 A1 | 5/2011 |
| WO | WO2012/054195 A2 | 4/2012 |
| WO | WO2014/039938 A1 | 3/2014 |
| WO | WO2014/195426 A1 | 12/2014 |
| WO | WO2014/201406 A1 | 12/2014 |

OTHER PUBLICATIONS

Jakab et al.; Tissue engineering by self-assembly and bio-printing of living cells; Biofabrication; 2(2); pp. 1-14; Jun. 2, 2010.
Perera et al.; Hydrophobic thiolation of pectin with 4-aminothiophenol: systhesis and in vitro characterization; AAPS PharmSci. Tech.; 11(1); Mar. 2010.
Marga; U.S. Appl. No. 14/615,354 entitled "Dried food products formed from cultured muscle cells," filed Feb. 5, 2015.
Munarin et al.; Pectin-based injectable biomaterials for bone tissue engineering; Biomacromolecules; 12(3); pp. 568-577; Mar. 14, 2011 (Abstract Only).
Marga et al.; U.S. Appl. No. 15/195,440 entitled "Fabrics and methods of making from cultured cells," filed Jun. 28, 2016.
Arding; Vegetarian cheese; Culture the word on cheese; 2 pgs.; Dec. 3, 2013; retrieved from the internet on Oct. 31, 2014; (http://culturecheesemag.com/ask-the-monger/vegetarian-cheese).
Barnard et al. "The medical costs attributable to meat consumption." Prev. Med. Nov. 1995, 24(6), 646-655.
Benjaminson et al. "In vitro edible muscle protein production system." (MPPS): Stage 1, fish. Acta. Astronaut. Dec. 2002, 51(12), 879-889.
Bhat et al. "Animal-free Meat Biofabrication." Am. J. Food Tech. Jun. 2011, 6(6), 441-459.
Bhat et al. "Tissue engineered meat—Future meat." Journal of Stored Products and Postharvest Research; Jan. 2011, 2(1), 1-10.
Boonen et al. "Essential environmental cues from the satellite cell niche: optimizing proliferation and differentiation." Am. J. Physiol. Cell Physiol. Jun. 2009, 296(6), C1338-C1345.
Boonen et al. "The Muscle Stem Cell Niche: Regulation of Satellite Cells During Regeneration." Tiss. Eng. Part B, Dec. 2008, 14(4), 419-431.
Datar et al. "Possibilities for an in vitro meat production system." Innovative Food Science and Emerging Technologies. Jan. 2010, 11(1), 13-22.
De Deyne, P. G. "Formation of sarcomeres in developing myotubes: role of mechanical stretch and contractile activation. " Am. J. Physiol. Cell Physiol. Dec. 2000, 279(6), C1801-C1811.
Dennis et al. "Excitability and contractility of skeletal muscle engineered from primary cultures and cell lines:" Am. J. Physiol. Cell Physiol. Feb. 2001, 280(2), C288-C295.
Dennis et al. "Excitability and isometric contractile properties of mammalian skeletal muscle constructs engineered in vitro." In vitro Cell Dev. Biol. Anim. May 2000, 36(5), 327-335.
Edelman et al. Commentary: In vitro-cultured meat production. Tissue Eng. May 2005, 11(5-6), 659-662.
Edelman, E.R. "Vascular Tissue Engineering: Designer Arteries" Circ Res, Dec. 1999, 85(12):1115-1117.
Engler, A. J., et al., "Myotubes differentiate optimally on substrates with tissue-like stiffness: pathological implications for soft or stiff microenvironments," J. Cell Biol. Sep. 2004, 166(6), 877-887.
European Food Safety Authority. The Community Summary Report on Trends and Sources of Zoonoses, Zoonotic Agents. Antimicrobial Resistance and Food borne Outbreaks in the European Union in 2005. EFSA J. May 2007, 94, 2-288.
Fonseca et al. "Slow fiber cluster pattern in pig longissimus thoracic muscle: Implications for myogenesis." Journal of Animal Science, Apr. 2003, 81(4), 973-983.
Gawlitta et al. The influence of serum-free culture conditions on skeletal muscle differentiation in a tissue-engineered model. Tissue Eng. Part A, Jan. 2008 14(1), 161-171.
Jakab et al. "Engineering Biological Structures of Prescribed Shape Using Self-assembling Multicellular Systems." Proc. Natl. Acad. Sci. USA, Mar. 2004, 101(9): 2864-2869.
Katsumata, M. "Promotion of intramuscular fat accumulation in porcine muscle by nutritional regulation." Anim. Sci. J., Feb. 2011, 82(1), 17-25.
Kosnik, et al., Tissue engineering skeletal muscle: In Guilak F. Butler DL, Goldstein SA and D. Mooney (Ed) Functional tissue engineering. New York: Springer-Verlag, Aug. 2004, pp. 377-392.
Langelaan et al., "Meet the new meat: tissue engineered skeletal muscle." Trends in Food Science & Technology Feb. 2010, 21(2), 59-66.
Langer et al.; Tissue Engineering; Science; 260(5110); pp. 920-926; May 1993.
Lee et al. "Multi-layered culture of human skin fibroblasts and keratinocytes through three-dimensional freeform fabrication," Biomaterials, Mar. 2009, 30(8): 1587-1595.
Levenberg, et al. "Engineering vascularized skeletal muscle tissue." Nat. Biotech. Jul. 2005, 23(7), 879-884.
Marga et al. "Developmental Biology and Tissue Engineering," Birth Defects Res C Embryo Today; 81(4):320-328; Dec. 2007.
Marga et al. "Toward engineering functional organ modules by additive manufacturing," Biofabrication, Jun. 2012, 4(2): 022001, 12 pages.
Mead et al. Food-Related Illness and Death in the United States. Emerg. Infect. Dis. Sep. 1999, 5(5), 607-625.
Mironov et al. "Bioprinting Living Structures." J. Mat. Chem., May 2007, 17(20): 2054-2060.
Niklason et al. "Advances in Tissue Engineering of Blood Vessels and Other Tissues." Transpl. Immunol., Dec. 1997, 5(4): 303-306.
Norotte et al. "Scaffold-free vascular tissue engineering using bioprinting." Biomaterials, Oct. 2009, 30(30): 5910-5917 (Author Manuscript, 16 pgs.).
Park, et al. "Effects of electrical stimulation in C2C12 muscle constructs." J. Tissue Eng. Regen. Med. Jul. 2008, 2(5), 279-287 (Author Manuscript, 17 pgs.).
Perez-Pomares et al. "Tissue fusion and cell sorting in embryonic development and disease: biomedical implications." Bioessays, Aug. 2006, 28(8): 809-821.
Pette, et al. "What does chronic electrical stimulation teach us about muscle plasticity?" Muscle Nerve, Jun. 1999, 22(6), 666-677.
Savadogo, et al. "Effects of grazing intensity and prescribed fire on soil physical and hydrological properties and pasture yield in the savanna woodlands of Burkina Faso." Agricult. Ecosys. Environ. Jan. 2007, 118(1-4), 80-92.
Smith et al., "Three-Dimensional BioAssembly Tool for Generating Viable Tissue-Engineered Constructs," Tissue Engineering, vol. 10, No. 9/10, pp. 1566-1576 (Sep. 2004).
Sommer et al.; Ascorbic acid modulates proliferation and extracellular matrix accumulation of hyalocytes; Tissue Eng; 13(6):1281-1289 (Abstract Only); Jun. 2007.
Thelen, et al. "Electrical stimulation of C2C12 myotubes induces contractions and represses thyroid hormone-dependent transcription of the fast-type sarcoplasmic-reticulum Ca2+-ATPase gene." Biochem. J. Feb. 1997, 321(Pt 3), 845-848.
Tuomisto, et al. "Environmental Impacts of Cultured Meat Production." Environ. Sci. Technol. Jun. 2011, 45(14), 6117-6123.
Lanza et al.; Principles of Tissue Engineering; 3rd. Ed.; Chapter 12 Principles of tissue culture and bioreactor design (III. Principles of bioreactor design); Academic Press; pp. 165-166; Aug. 21, 2007.
Aldhous; Print me a heart and a set of arteries; New Scientist; Apr. 23, 2006; retrieved from the internet on Jun. 3, 2015 (http://organprint.missouri.edu/www/news/NewScientistApril2006.pdf).
Hopkins et al.; A vegetarian meat: could technology save animals and satisfy meat eaters?; J. Agric. Environ. Ethics.; 21; pp. 579-596; Jul. 11, 2008; retrieved from the internet on Jun. 2, 2015 (http://

(56) References Cited

OTHER PUBLICATIONS foodethics.univie.ac.at/fileadmin/user_upload/inst_ethik_wiss_dialog/Hopkins_P._2008_Veg_Meat_and_In_Meat.pdf).

Matsuda et al.; Tissue engineering based on cell sheet technology; Adv. Materials; 19(20); pp. 3089-3099; Oct. 17, 2007.

Sekine et al.; Myocardial tissue reconstruction: the cell sheet engineering approach; Inflammation and Regeneration; 27(3); pp. 171-176; May 2007.

Yang et al.; Cell sheet engineering: recreating tissues without biodegradable scaffold; Biomaterials; 26(33); pp. 6415-6422; Nov. 2005.

Bian et al.; Engineered skeletal muscle tissue networks with controllable architecture; Biomaterials; 30(7); pp. 1401-1412; Mar. 2009.

Meyer et al.; Collagen fibres by theromoplastic and wet spinning; Materials Science and Engineering; C; 30(8); pp. 1266-1271; Oct. 2010.

Shepherd et al.; Effect of fiber crosslinking on collagen-fiber reinforced collagen-chondroitin-6-sulfate materials for regenerating load-bearing soft tissues; Journal of Biomedical Materials Research; 101A(1); pp. 176-184; Jan. 2013.

Thibault et al.; Chain association of pectic molecules during calcium-induced gelation; Biopolymers; 25; pp. 455-468; 1986 (year of pub. sufficiently earlier than effective US filed and any foreign priority date).

Wu et al.; Fiber formation by dehydration-induced Aggregation of Albumin; J. Appl. Polym. Sci.; 129(6); pp. 3591-3600; Sep. 15, 2013.

\* cited by examiner

EDIBLE AND ANIMAL-PRODUCT-FREE MICROCARRIERS FOR ENGINEERED MEAT

CROSS REFERENCE TO RELATED APPLICATIONS

This patent application claims priority to U.S. Provisional Patent Application No. 61/877,865, filed on Sep. 13, 2013, titled "EDIBLE MICROCARRIERS FOR ENGINEERED MEAT," which is herein incorporated by reference in its entirety.

This application may be related to one or more of: U.S. patent application Ser. No. 13/558,928, now U.S. Pat. No. 8,703,216, filed Jul. 26, 2012, titled "ENGINEERED COMESTIBLE MEAT," and PCT Application No. PCT/US2013/058684, filed Sep. 9, 2013, titled "SPHERICAL MULTICELLULAR AGGREGATES WITH ENDOGENOUS EXTRACELLULAR MATRIX," now Publication No. WO 2014/039938. Each of these patents and patent application are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are edible (e.g., fit for human consumption) microcarriers for culture and growth of cells and the formation of engineered meats, as well as methods of making and using them to form engineered meat products.

BACKGROUND

The human body needs protein for growth and maintenance. Aside from water, protein is the most abundant molecule in the body. According to U.S. and Canadian Dietary Reference Intake guidelines, women aged 19-70 need to consume 46 grams of protein per day, while men aged 19-70 need to consume 56 grams of protein per day to avoid deficiency. This recommendation, however, is for a sedentary person free of disease. Protein deficiency can lead to reduced intelligence or mental retardation as well as contribute to the prevalence of diseases such as kwashiorkor. Protein deficiency is a serious problem in developing countries, particularly, in countries affected by war, famine, and overpopulation. Animal sources of protein, such as meat, are often a source of the complete complement of all the essential amino acids in adequate proportions.

The nutritional benefits of meat are tempered by potential associated environmental degradation. According to a 2006 report by the Livestock, Environment And Development Initiative, entitled Livestock's Long Shadow—Environmental Issues and Options, the livestock industry is one of the largest contributors to environmental degradation worldwide, and modern practices of raising animals for food contributes widely to air and water pollution, land degradation, climate change, and loss of biodiversity. The production and consumption of meat and other animal sources of protein is also associated with the clearing of rainforests and species extinction. Accordingly, there is a need for a solution to demands for alternative to meat produced from live animals.

The inventors have previously described engineered meats and methods of making engineered meats using cultured cells. See, e.g., U.S. Pat. No. 8,703,216, titled "ENGINEERED COMESTIBLE MEAT," previously incorporated by reference in its entirety. However, bio-manufacturing processes aimed at building extended tissue constructs that require large numbers of adherent cells face the difficulty of growing these cells (to the billions to trillions) efficiently and cost effectively. One way to produce large quantities of such cells is to use microcarriers in bioreactor-based systems. Unfortunately, commercially available microcarriers are not appropriate for use in a comestible meat product, as the carrier is not typically edible or fit for consumption. Such commercially available microcarriers are typically composed of natural products (e.g., cross-linked dextran, collagen, alginate) or synthetic materials (glass, polystyrene, acrylamide). Typically, commercially available microcarriers are not edible, since they are made of synthetic materials. Further, commercially available microcarriers are not made from animal-product-free (e.g., they are made from animal products), and/or may be made from bacterial products (e.g., collagen, dextran) which raise issues of contamination or allergy making them unsuitable for eating. Thus, such microcarriers may have to be separated from the cultured cells in order to form a viable meat product. For example, existing or proposed microcarriers may be composed either of synthetic polymers (Polystyrene, poly(L-lactide), poly(N-isopropylacrylamide, PLGA) or of animal (or bacterial) derived polymers (e.g., gelatin, recombinant gelatin, dextran). None of these microcarriers would fit our need because they are not edible (synthetic) or safe for consumption (e.g., dextran, recombinant gelatin) with a substantial risk of bacterial contaminant and/or they require killing animals (e.g., gelatin).

In general, microcarriers may increase the useful surface-area-to-volume ratio considerably compared to 2D cell culture systems. However, because harvesting healthy cells separated from the microcarriers can be challenging, such approaches are used mainly in applications where the cells are not the final product such as virus and metabolite production. See, e.g., U.S. Pat. No. 7,270,829, which describes the use of microcarriers such as Cytodex 1 and 3 beads and the use of EDTA, trypsin, and centrifugation to remove the microcarriers from the cultured cells.

A developing field within biofabrication/biomanufacturing aims at producing animal products for human consumption (i.e., cultured meat) without killing animals. As such it shares the challenge of producing large quantities of cells and raises other challenges for microcarriers. Thus, it would be beneficial to develop a new type of microcarrier with characteristics that may include: (1) the microcarrier should be edible and digestible so they can be incorporated into the final comestible product (e.g., no synthetic material, no toxic chemical used for their formation); (2) the microcarriers need to have been formed of an animal-free composition to assure that the final product retains its no animal kill character (e.g., no collagen, gelatin, etc.); (3) production of the microcarriers needs to be scalable and low cost; and (4) the microcarriers may bring additional features to the final product (e.g., gustatory benefit, mouthful feeling, health benefits i.e., higher content of fibers, etc.).

Described herein are edible microcarriers that may meet some or all of these criteria and may be used to form comestible meat products using cell culture methods, as well as methods of making the, methods of making engineered meat products with them, and the resulting engineered meat.

While microcarriers for cell culture have been described before, previously described microcarriers are typically used as substrates for cell culture and are not part of the final product (i.e. cells or cell secreted proteins). Further, these technologies are often designed as injectable formulations for therapeutic applications. The use of edible microcarriers composed entirely of animal-product-free ("animal-free") molecules for cell culture is a novel platform technology for meat production.

SUMMARY OF THE DISCLOSURE

The present invention relates to edible microcarriers appropriate for use in forming engineered meat products from cultured cells, as well as methods of forming edible microcarriers (and/or fortified and/or flavored microcarriers), and methods of forming engineered meat using incorporating the edible microcarriers, and engineered meats formed using them. The edible microcarriers produced by the methods described here may provide animal-product-free option for large-scale cell culture.

The microcarriers described herein may be produced from naturally occurring polymers (e.g., pectin and cardosin) already used by the food industry.

In general, the microcarriers described herein may be used to culture (in suspension) cells, and particularly muscle (e.g., smooth muscle) cells to form an engineered meat. The methods described herein also include methods of fabricating edible and animal-product-free microcarriers. As used herein the term "microcarriers" includes "microsponges" and microcarriers. The microcarriers may be porous, hollow, or solid. These microcarriers may be of any appropriate size.

The microcarriers described herein may be formed of materials that are derived only from vegetable and/or non-animal sources ("animal-product-free" or "animal-free" microcarriers). For example, the microcarriers described herein may be prepared by lyophilization of cross-linked hydrogels using animal-product-free materials: plant derived polysaccharides and polypeptides.

The edible microcarriers described herein are appropriate for the biofabrication of animal-product-free products for human consumption. Although the microcarriers and methods of forming and using them described herein are primarily directed to comestible engineered meat products, such microcarriers may also find application in animal (and particularly human) cell therapy, where it is desired to do cell expansion in the absence of animal-derived products. In this respect, it may be desirable to form larger microcarriers (e.g., sponges or scaffolds) made according to the methods described herein that may be used for tissue engineering.

For example, described herein are edible animal-product-free microcarriers for use in forming an engineered meat product. The edible microcarrier may comprise a body comprising cross-linked pectin and an RGD-containing polypeptide, wherein the edible microcarrier is configured for culturing muscle cells in a bioreactor. As used herein the edible microcarrier may be configured for culturing muscle cells in a bioreactor based on the size and/or shape of the edible microcarriers. For example, the edible microcarrier body may have a diameter of between about 2 mm and about 0.05 mm in diameter, or between about 1 mm and about 0.1 mm in diameter. The body may be porous.

In some variations, the pectin comprises thiol-modified pectin, PTP. The RGD-containing polypeptide may comprise cardosins, such as cardosin A. The cardosin may be thiolated. As described herein, the microcarrier may be at least partially formed of a polypeptide having a cell attachment region/motif, such as an RGD motif. Thus, cardosin (e.g., cardosin A or other cardosin variations), which contains an RGD motif may be used. In addition or in the alternative, a synthetic polypeptide including a cell binding motif such as an RGD motif may be used.

The edible microcarrier may also include one or more additive including (but not limited to): a flavoring, a flavor enhancer, a colorant, a color enhancer, and a nutritional enhancer. Any known flavoring/flavorant, or combination of these, may be used, including meat flavors: such as pork (e.g., 2-pyridine methanethiol), chicken, beef, veal, turkey, lamb, etc.; fat and oil flavors (e.g., flavors corresponding one or more of: fried fat, lard, tallow, chicken fat, bacon fat, turkey fat, pork fat, beef fat, sesame oil, olive oil, etc.); dairy flavors (cheese, cream, milk, sour cream, etc.) and the like. See, e.g., US-2014-0205729, herein incorporated by reference in its entirety.

Also described herein are engineered meat products including any of the edible microcarriers described herein. For example, an engineered meat product may include: a body having a volume formed of a plurality of edible microcarriers, wherein the edible microcarriers comprise a cross-linked pectin and an RGD-containing polypeptide, a plurality of cells at least partially adhering to the microcarriers forming a multicellular microcarrier units, and a plurality of at least partially fused multicellular microcarrier units. As used herein, a multicellular microcarrier unit typically includes an edible microcarrier having a plurality of cells, such as smooth muscle cells, growing thereon. A plurality of multicellular microcarriers may be fused by allowing the multicellular microcarriers to contact each other so the cells on different microcarriers cohere (and/or adhere to the microcarriers). The plurality of edible microcarriers may comprise cross-linked thiol-modified pectin and cardosin. The plurality of at least partially adhering cells may comprise any appropriate cells, for example, smooth muscle cells.

Also described herein are methods of forming an edible microcarrier for use in forming an engineered meat product. Any of these methods may include: cross-linking a pectin and an RGD-containing polypeptide to form a pectin/RGD-containing polypeptide hydrogel; and forming microbeads from the pectin/RGD-containing polypeptide hydrogel.

The method may also include lyophilizing the pectin/RGD-containing polypeptide hydrogel.

In some variations, cross-linking a pectin and an RGD-containing polypeptide to form a pectin/RGD-containing polypeptide hydrogel comprises cross-linking pectin-thiopropionylamide (PTP) and cardosin A.

The method may also include: creating pectin-thiopropionylamide (PTP) by derivatization of pectin with cystamine, wherein cross-linking the pectin and the RGD-containing polypeptide comprises cross-linking the PTP with the RGD-containing polypeptide. In some variations, the method includes: thiolating a cardosin (e.g. cardosin A) polypeptide, wherein cross-linking the pectin and the RGD-containing polypeptide comprises cross-linking the pectin with the thiolated cardosin (e.g. cardosin A) polypeptide.

Forming microbeads may comprise forming porous microbeads, forming microbeads having a diameter of between about 3 mm and about 0.02 mm, about 2 mm and about 0.05 mm, or between about 1 mm and about 0.1 mm.

For example, described herein are methods of forming an edible microcarrier for use in forming an engineered meat product, the method comprising: creating pectin-thiopropionylamide (PTP) by derivatization of pectin with cystamine; thiolating a cardosin polypeptide; cross-linking the PTP and thiolated cardosin to form a hydrogel; lyophilizing the hydrogel of cross-linked PTP and cardosin; and forming microbeads from the cross-linked PTP and cardosin.

In any of these methods, one or more of: a flavor enhancer, a colorant, a color enhancer, and a nutritional enhancer may be added when forming the edible microcarrier.

BRIEF DESCRIPTION OF THE DRAWINGS

FIG. 1 is a schematic of one example of microcarrier formation. In this example, the PTP-cardosin solution passes through the bead generator. The beads drop into the GSSG solution at pH 8.0 (light blue). A shell forms rapidly around the droplet so they stay separate as cross-linking continues.

FIG. 6A shows the approximately 2 mm diameter piece of the pectin/RGD-containing polypeptide hydrogel shortly after seeding with muscle cells. Over time, as progressively shown in FIGS. 6B, 6C and 6D, the hydrogel becomes covered and invaded by the muscle cells, making the hydrogel increasingly opaque (showing the boundaries of the hydrogel, as is apparent in FIG. 6D.

FIG. 7A shows a hematoxylin and eosin stain staining through a section, in which cell nuclei (muscle cell nuclei) are punctually stained around the perimeter of the hydrogel microcarrier and have invaded into the inside of the hydrogel microcarrier. This is confirmed by the section in FIG. 7B that has been stained for alpha smooth muscle cell (SMC) actin, showing SMC actin around the perimeter and within the body of the hydrogel microcarrier.

In FIG. 9A, two cellularized microcarriers as placed adjacent to each other and allowed time to fuse, as shown in FIGS. 9B and 9C. After a few hours, the two microcarriers have partially fused (FIG. 9B) and by 24 hours, have significantly fused (FIG. 9C).

FIG. 10A shows a hydrogel of 1% w/w CardosinA-4SH:PectinCysSH. FIG. 10B is an example of the ultrastructure of a hydrogel of 2.5% w/w CardosinA-4SH:PectinCysSH. FIG. 10C is an example of the ultrastructure of a hydrogel of 5% w/w CardosinA-4SH:PectinCysSH. The scale bar (bottom of each image) is 500 µm.

DETAILED DESCRIPTION

In general, described herein are edible microcarriers (including microbeads), methods of making them, and methods of using them to from edible meat products from cultured cells. The edible microcarrier is generally formed of an animal-product-free material or materials, meaning the material or materials are derived from non-animal sources. The edible microcarrier is typically formed of a material that is edible (nutritious and/or safely digestable in large quantities) and a material having a cell-attachment domain or motif. In some variations the edible microcarrier is formed, at least in part, by a cross-linked structure of polysaccharide and a polypeptide including a cell-attachment motif (such as RGD). As a specific example, the edible microcarrier may be formed by cross-linking a pectin (e.g., thiol-modified pectin, PTP) and an RGD-containing polypeptide such as the cardosins.

Any of the edible microcarriers described herein may also include additional (supplemental) material, including additives for enhancing the flavor, appearance and/or nutritive value of the edible microcarrier, and the resulting engineered meat fabricated using the edible microcarriers. Any appropriate additive may be included.

Figure 3A:
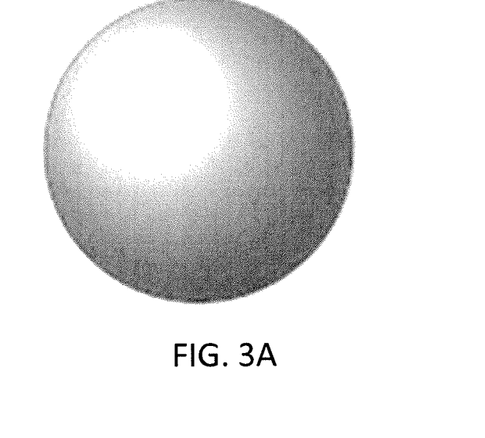
FIGS. 3A-3C are examples of animal-product-free microcarriers.
Figure 3B:
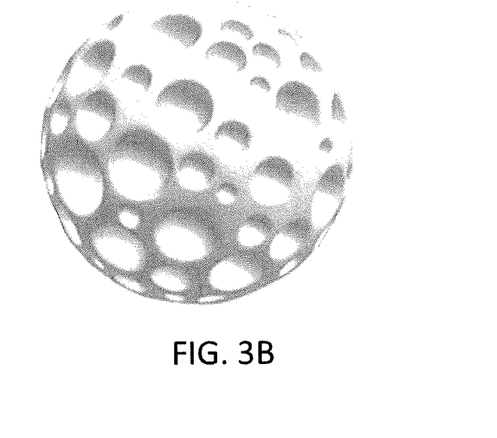
Figure 3C:
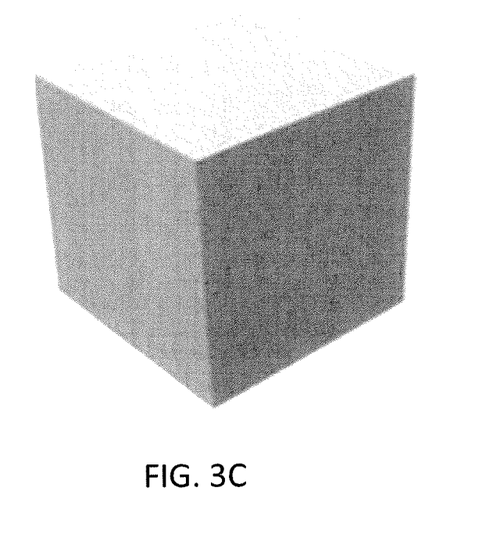

The edible microcarriers described herein include edible microsponges and/or edible microbeads. These microcarriers may be porous (e.g., sponge-like) or smooth. The edible microcarriers for use in forming engineered meat may be formed into microbeads/microparticles for use in a bioreactor, and may be between about 3 mm and about 0.02 mm in diameter (e.g., between about 2 mm and about 0.05 mm, between about 1 mm and 0.1 mm, between about 1 mm and 0.3 mm, etc.). For example, the microbeads may be around 0.5 mm in diameter. The size may represent an average or median size, or a maximum/minimum size. The shape of the microcarriers may be regular (e.g., spherical, rounded, etc.) or irregular. For example, FIGS. 3A to 3C illustrate variations of microcarriers having spherical (FIG. 3A) and cubic (FIG. 3C) shapes. Any of these shapes may be porous (e.g., FIG. 3B shows a spherical and porous microcarrier).

Method of Making Edible Microcarriers

Edible microcarriers may be made by any appropriate process, including molding, extrusion, injection, infusion, etc. of the material forming the edible microcarrier.

Edible, highly porous microcarriers that can be used in cell culture techniques with the bioreactors and remain integral part of the final engineered comestible product (i.e. engineered meat) may be formed from edible animal-free materials. Such edible microcarriers may be prepared by forming the components, polysaccharide and polypeptide, into a cross-linked hydrogel, lyophilization of cross-linked hydrogel, and shaping (e.g., cutting) the lyophilized gel into appropriate sizes.

One example of a method of forming an edible microcarrier includes forming the principle components of the microcarrier, the polysaccharide and polypeptide. For example, one class of polysaccharides that may be used are low methyl (LM) esterified pectins, an abundant plant derivate already used in food. For example the LM esterified pectin used may be derived to form a thiol-modified pectin (PTP) that is 100% edible and digestible. Thiol functions are found in garlic and onion. One class of polypeptides that may be used includes the cardosins. Cardosins are aspartic proteinases that may be extracted from *Cynara cardunculus* L., and that contain cell binding RGD motifs that promote cell attachment. For example, cardosins may be derivatized through their cysteines to introduce new thiol groups. Cardosins are already used by the food industry, specifically in cheese-making, (see, e.g., http://www.culturecheesemag-.com/ask_the_monger/vegetarian_cheese). In other variations, the cardosins could be substituted (or supplemented) by another polypeptide, including a synthetic peptide, with an RGD sequence that is edible.

In some variations, PTP and derivatized cardosins may be cross-linked through oxidative disulfide bond formation. In this example, PTP-cardosin hydrogel may be cross-linked under mild conditions using (the oxidized form of) glutathione disulfide (GSSG) obtained by bubbling air into a solution of high-grade glutathione (GSH, e.g., such as health-food store grade glutathione). Additional additive (e.g., flavorings, nutrients, colors, etc.) may be added as well.

The hydrogel may then be shaped or formed. For example, macrosponges (1-5 mm thick) may be formed by casting the hydrogel solution in molds and allow the cross-linking to continue in air overnight, then lyophilized and cut to desired dimension (larger sponges for tissue engineering applications, small fragments of ~0.5 mm for bioreactor applications).

Figure 1:
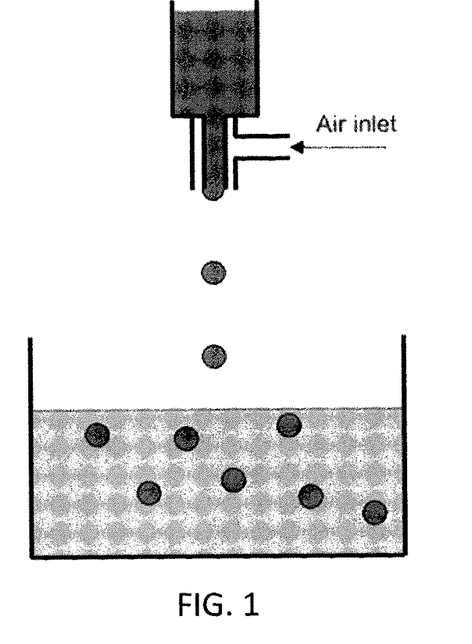

For large scale production of microbeads, a coaxial airflow bead-making device (FIG. 1) may be used. For example, beads may be composed of the modified cross-linked pectin and cardosin hydrogel (e.g., PTP-cardosin hydrogel). FIG. 1 illustrates one example of coaxial airflow to form microbeads from the hydrogel.

Figure 2:
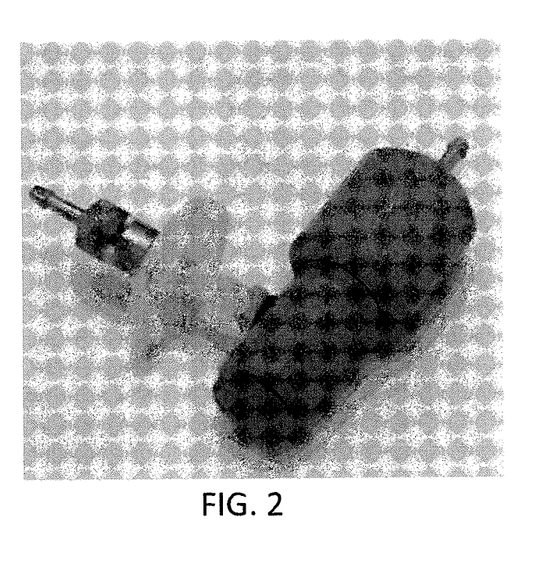
FIG. 2 is a picture of a Nisco coaxial airflow bead generator, which may be used in the methods of forming edible microbeads described herein.

In one variation, a method of forming microcarriers of PTP and cardosins may be performed by steps that may include: (1) Creating pectin-thiopropionylamide (PTP) by derivatization of pectin with cystamine at two levels of modification (e.g., 10%, 25%) followed by reduction. (2) Introduction of new thiol groups by derivatization of cardosin (e.g. cardosin A). (3) Development of GSSG cross-linked hydrogel in slab format with PTP and thiolated cardosins. The pH, concentration, and the like may be optimized for forming the hydrogel; additives (coloring, nutrients, etc.) may also be included. The hydrogel may be lyophilized. (4) Creating beads using a bead generator such as the Nisco coaxial airflow bead generator (shown in FIG. 2) and lyophilize the GSSG hydrogel sphere to obtain the microcarriers.

In use, the microcarriers may be used to culture cells, for example smooth muscle cells, in large amounts for forming engineered meats. Other cells types may also be used on the microcarriers in addition to (or instead) of the muscle cells, including satellite cells, etc.

For example, microcarriers as described herein may be seeded with muscle cells (e.g., smooth muscle cells) and cultured. In particular, the cells and microcarriers may be cultured in a bioreactor. The resulting cultures may be grown to a desired level and used directly to form an engineered meat (e.g. by the fusion of the microcarriers), without the necessity to separate or otherwise remove the microcarriers.

Figure 4A:
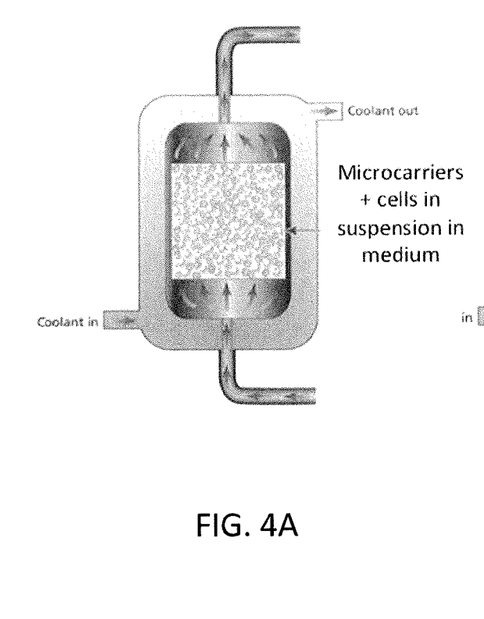
FIGS. 4A-4B illustrates the use of a bioreactor to grow cellularized microcarriers as described herein.
Figure 4B:
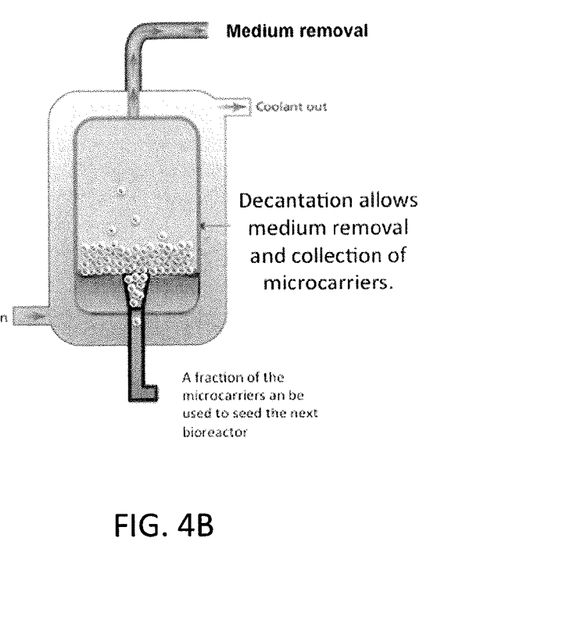

In some variations, the edible microcarriers with cultured cells may be formed directly into the engineered meat product after incubation in the bioreactor for an appropriate time to allow cells to grow (e.g., 12 hours, 24 hrs, 2 days, 3 days, 4 days, 5 days, 6 days, 7 days, 8 days, 9 days, 10 days, 11 days, 12 days, etc.). FIGS. 4A and 4B illustrate one variation of the use of a bioreactor to form cellularized microcarriers. In general a cellularized microcarrier is a microcarrier (e.g., edible, animal-product-free) onto which cells (e.g., muscle cells) have adhered and grown. In some variations the cells on the microcarrier may be grown to confluence, though this is not necessary. Further the cells may fuse on and/or in the surface of the microcarrier. The edible microcarriers (onto which cells, e.g. smooth muscle cells attach) may form multicellular bodies, as previously described. See, e.g., US 2013/0029008, previously incorporated by reference. The multicellular bodies (e.g., cellularized microcarriers) may be at least partially fused, and therefore include multiple edible microcarriers within a multicellular body. In some variations the edible microcarriers with attached cells may be combined into an appropriate shape to form the edible meat product, and allowed to fuse, or at least partially fuse, into the engineered meat product. The volume of the body forming the edible engineered meat product may be grown sequentially in this manner (e.g., by sequential addition of microcarriers). Alternatively, the microcarriers and attached cells (cellularized microcarriers) may be formed into multicellular bodies and used to form engineered meat from the multicellular bodies, as previously described, including the formation of layers which may then be stacked onto each other.

In any of these examples, the resulting meat product may have a volume composed of cellularized microcarriers that are at least partially fused, comprising muscle cells (e.g., smooth muscle cells) and a plurality of edible microcarriers as described herein.

Figure 5:
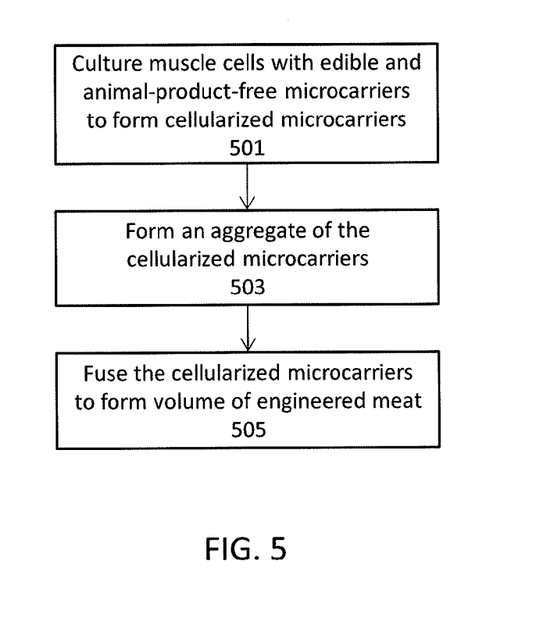
FIG. 5 is a schematic illustration of one method of forming an engineered meat using the edible microcarriers described herein.

For example, as illustrated in FIG. 5, any of the methods of forming engineered meat described herein may include: culturing a plurality of muscle cells on edible and animal-product-free microcarriers in suspension to form a plurality of cellularized microcarriers 501, wherein the animal-product-free microcarriers comprise a hydrogel of cross-linked pectin and RGD-containing polypeptides; forming an aggregate of the cellularized microcarriers 503; and at least partially fusing the cellularized microcarriers to form a volume of engineered meat 505.

Cells may generally be cultured with any of the edible microcarriers described herein in a suspension, including in a bioreactor (see, e.g., FIGS. 4A and 4B). For example, cells may be seeded into the media along with the edible microcarriers and allowed to contact, adhere to, and grow on the appropriate edible microcarrier. For example, culturing may include culturing a plurality of muscle cells on edible and animal-product-free microcarriers comprising a hydrogel of thiol-modified pectin (PTP) and cardosin. In some variations, culturing comprises culturing a plurality of muscle cells on edible and animal-product-free microcarriers wherein the animal-product-free microcarriers comprise a flavoring, a flavor enhancer, a colorant, a color enhancer, and a nutritional enhancer.

Once the cells have divided and grown sufficiently on microcarrier, forming a 'cellularized microcarrier' in which the edible microcarrier is at least partially covered by (and/or filled with) cells, and the cellularized microcarriers may be positioned and allowed to fuse to form the engineered meat product. In some variations a cellularized microcarrier is covered (e.g., greater than 50% covered, greater than 60% covered, greater than 70% covered, greater than 80% covered, greater than 90% covered, covered to confluency) with the cells. As described in U.S. Pat. No. 8,703,216, previously incorporated by reference in its entirety, the cells used may be one or more types, including in particular muscle cells. Microcarriers covered to the appropriate degree with cells (e.g., >50%, >60%, >70%, >80%, >90%, etc.) may be referred to as cellularized microcarriers. The cellularized microcarriers may then be used to form an aggregate from which the engineered meat is formed. For example, an aggregate of the cellularized microcarriers may be formed by placing cellularized microcarriers immediately adjacent each other.

For example, the cellularized microcarriers may be placed in contact with each other so that the cells on adjacent (immediately adjacent) cellularized microcarriers may contact each other and fuse. For example, forming the aggregate may comprise placing a plurality of cellularized microcarriers adjacently onto a support substrate. The support substrate may be a plate, an agar substrate, form/mold, or a suspension (e.g., the bottom of a flask or dish). In some variations the concentration of the cellularized microcarriers may be increased to encourage the formation of an aggregate of the cellularized microcarriers. Typically, the aggregate of cellularized microcarriers may non-exclusively include cellularized microcarriers in culture medium. In the planar/layered methods and devices for forming (e.g., U.S. Pat. No. 8,703,216) the cells must be cultured on the microcarriers and washed on the cellularized microcarrier and then used to form an aggregate. For example, a solution of cellularized microcarriers may be spun in a centrifuged to pellet the cellularized microcarriers to form the aggregate. As mentioned, any appropriate cell type may be used. For example, the cells may be non-human myocyte cells (including smooth muscle cells).

In some variations, forming an aggregate may comprise placing a plurality of the cellularized microcarriers adjacently onto a planar support substrate; fusing (e.g., allow to fuse) said plurality of cellularized microcarriers to form a first planar layer; and stacking more than 5 additional planar layers onto the first planar layer; wherein at least partially fusing the cellularized microcarriers to form the volume of engineered meat comprises fusing the layers to form the volume of engineered meat.

In some variations the engineered meat volume may be formed immediately from a large aggregate of cellularized that are combed together at once, or in a few sequential steps. However, in some variations the engineered meat volume is formed sequentially, by sequentially adding additional of cellularized microparticles, or of aggregates of microparticles (either already fused or unfused), including layers. For example, stacking more than 5 additional planar layers (e.g. stacking more than 6, more than 7, more than 8, more than 9, more than 10, more than 15, more than 20, more than 25, more than 30, etc.; or alternatively, stacking between 5 and 100, between 10 and 100, between 10 and 90, between 10 and 80, between 20 and 100, between 20 and 90, between 20 and 80, etc.) may comprise stacking more than 10 additional planar layers so that a majority of cells within the volume of engineered meat have died after fusion of the additional planar layers is at least partially complete.

Once the engineered meat is formed, it must be kept sterile (free from bacterial or other contamination) without the use of antibiotics, drugs, or the like, as such may impact the final meat product below. For example, the volume of engineered meat may be frozen after it is formed.

As mentioned, in general, the method of forming the engineered meat may include forming the aggregate by laying a plurality of cellularized microcarriers having a diameter of between about 0.05 mm and about 3 mm adjacently onto a planar support substrate. This diameter may be the diameter of the microparticle after cellularization (e.g., reflecting a larger diameter due to cellular growth on the outside of the mode.

For example, any of these methods may include sequentially adding additional cellularized microcarriers onto the volume of engineered meat and allowing the additional cellularized microcarriers to at least partially fuse with the volume of engineered meat. During this formation process for the volume of engineered meat, the cells within the forming volume may be isolated from any media (nutrients) and may therefore start to die prior to full fusion of the material. For example, any of these methods may include sequentially adding additional cellularized microcarriers (or volumes such as sheets or layers of cellularized microcarriers) onto the volume of engineered meat and allowing the additional cellularized microcarriers to at least partially fuse with the volume of engineered meat so that a majority of cells within the volume of engineered meat have died after fusion of the additional cellularized microcarriers is at least partially complete.

For example, in one variations a method of forming engineered meat described herein, the method includes: culturing a plurality of muscle cells on edible and animal-product-free microcarriers in suspension to form a plurality of cellularized microcarriers, wherein the animal-product-free microcarriers comprise a hydrogel of thiol-modified pectin (PTP) and cardosin (which may include additional flavorants, collorants, supplements, etc.); forming an aggregate of the cellularized microcarriers; at least partially fusing the cellularized microcarriers to form a volume of engineered meat; and adding additional cellularized microcarriers onto the volume of engineered meat and allowing the additional cellularized microcarriers to at least partially fuse with the volume of engineered meat so that a majority of cells within the volume of engineered meat have died after fusion of the additional cellularized microcarriers is at least partially complete.

Also described herein are engineered meat products. In general, these engineered meat products may include a comestible body having a volume formed of a plurality of cellularized microcarriers, wherein each cellularized microcarrier includes an edible microcarrier comprising a hydrogel of a cross-linked pectin and an RGD-containing polypeptide and a plurality of muscle cells attached to the edible microcarrier, further wherein the cellularized microcarriers are at least partially fused to each other. The edible microcarrier may include a cross-linked thiol-modified pectin and cardosin. In some examples, the plurality of muscle cells comprise smooth muscle cells. As mentioned, these edible microcarriers may comprise a flavoring, a flavor enhancer, a colorant, a color enhancer, and a nutritional enhancer.

In general, the edible microcarrier mentioned herein may have a diameter of between about 0.05 mm and about 3 mm. In any of the methods and apparatus claims, the edible microcarrier may be animal-product-free.

Also described herein are methods of forming an edible and animal-product-free microcarrier for use as part of an engineered meat product, also discussed above the method comprising: cross-linking a pectin and an RGD-containing polypeptide to form a pectin/RGD-containing polypeptide hydrogel; and forming microbeads from the pectin/RGD-containing polypeptide hydrogel having a diameter of between about 0.05 mm and about 3 mm. In addition, further comprising lyophilizing the pectin/RGD-containing polypeptide hydrogel. For example, cross-linking a pectin and an RGD-containing polypeptide to form a pectin/RGD-containing polypeptide hydrogel comprises cross-linking pectin-thiopropionylamide (PTP) and cardosin. The method may generally include creating pectin-thiopropionylamide (PTP) by derivatization of pectin with cystamine, wherein cross-linking the pectin and the RGD-containing polypeptide comprises cross-linking the PTP with the RGD-containing polypeptide. Further, the method may include thiolating a cardosin polypeptide, wherein cross-linking the pectin and the RGD-containing polypeptide comprises cross-linking the pectin with the thiolated cardosin polypeptide.

As mentioned above, any of the microbeads described herein may be porous (partially or completely). The method of forming microbeads may comprise forming microbeads having a diameter of between about 1 mm and about 0.1 mm.

For example, described herein is a method of forming an edible and animal-product-free microcarrier for use in forming an engineered meat product, the method comprising: creating pectin-thiopropionylamide (PTP) by derivatization of pectin with cystamine; thiolating a cardosin polypeptide; cross-linking the PTP and thiolated cardosin to form a hydrogel; lyophilizing the hydrogel of cross-linked PTP and cardosin; and forming microbeads from the cross-linked PTP and cardosin. The method may also include adding one or more of: a flavoring, a flavor enhancer, a colorant, a color enhancer, and a nutritional enhancer.

An edible microcarrier that is free of animal products and that is configured for culturing muscle cells to form an engineered meat product may include: a body comprising a hydrogel of cross-linked pectin and an RGD-containing polypeptide, wherein the body is between about 3 mm and about 0.05 mm in diameter. The pectin may comprise thiol-modified pectin (PTP), and the RGD-containing polypeptide may comprise a cardosin. As mentioned above, the body may have a diameter of between about 3 mm and about 0.05 mm in diameter (e.g., between 2 mm and 0.05 mm, between about 1 mm and 0.05 mm, between about 2 mm and 0.1 mm, between about 3 mm and 0.1 mm, etc.). For example, the body may have a diameter of between about 1 mm and about 0.1 mm in diameter. The edible microcarrier body may be porous. The pores may be a variety of shapes, sizes and depths into the microcarrier. For example, the pores may generally be larger than the thickness of a cultured cell (e.g., in a range of opening diameter of between about 1 µm to 50 µm (e.g., between about 1 µm and about 40 µm, between about 1 µm and about 30 µm, etc.). Any of the edible microcarriers described herein may include one or more additives, such as of one or more: flavoring, flavor enhancer, colorant, color enhancer, and nutritional enhancer.

For example, an edible microcarrier that is free of animal products and that is configured for culturing muscle cells to form an engineered meat product may have a body comprising a hydrogel of thiol-modified pectin and cardosin, wherein the body is between about 3 mm and about 0.05 mm in diameter.

Advantages

Cells used for the engineered meats described herein, which may include, e.g., smooth muscle cells, satellite cells, fibroblasts, adipocyte progenitor cells, etc., are typically anchorage-dependent, and require a surface to attach to. Current cell culture methods may use flasks, tubes and/or plates (e.g., cellStacks or hyperflasks) to provide a surface onto which the cells may adhere and grow, which may result in a process for growing the cells and making an engineered meat that is manual labor intensive, requires enzymes to detach the cells from the surface and large volume of medium to yield the cells. Most of the material is single use, thus generating waste. Expansion of the cells is achieved by seeding more plates with larger number of layers as the culture progresses.

The microcarriers described herein may provide large surface area/volume for cell attachment, particularly if they are micro- or macro-porous. The initial step of cell expansion may include mixing the cells and the microcarriers in a small bioreactor (e.g., FIG. 4A). The cells attach and multiply on the microcarriers that are maintained in suspension. When the maximal growth is achieved, the microcarriers may be collected and can be used for seeding a bioreactor of larger volume, or may be used directly if sufficient amounts are grown. The cells don't have to be separated from the microcarriers, since the microcarriers described herein are edible, eliminating the use of enzymes and the risk to damage the cells. The process is time efficient and easy to scale up. Industrial bioreactors can achieved large volumes (e.g., greater than 1000 L) in less space than traditional cell culture incubators.

When a single cell suspension is collected from the cellstacks or the hyperstacks, cells may be seeded on the top of a multi well mold (e.g., a 1470 wells/mold) made of agarose. As mentioned, yielding the cells by this method is a time consuming process and requires enzyme and additional medium. Preparing the molds is also time consuming and adds to the cost (e.g., fabrication of the metallic master mold and agarose). The aggregates form by self-assembly that can require 24 to 48 hours in an incubator in presence of medium, adding additional costs. The aggregates obtained by this method are typically completely (100%) made of cells. Obtaining aggregates of similar diameter using this method requires training and practice. Yielding the aggregates at the end of the incubation also requires inversion of the mold and vibration to liberate the aggregates from the well. This step holds the risk for contamination with some agarose fragments and loss of (some) aggregates. Typically, for this method, in order for the aggregates to be healthy and able to fuse in the tissue engineering process, their radius shouldn't exceed the diffusion limit of the medium. For example, 500 micrometer (diameter) aggregates typically performed properly.

In contrast, the use of microcarriers allows forming the cellular aggregates (these are not purely cellular, as they are composed of cells and the material of the edible microcarrier) simultaneously with the cell expansion offering a less time consuming and more efficient method to obtain the bio-units for the tissue engineering step. Cells will attach to the microcarriers, expand on the surface and in the pores of the microcarrier, and can be collected by decantation at the end of the expansion phase. Microcarriers can generally be spherical or any other geometry, for example cube, cross, etc., and the sizes of the microcarriers (and thus the sizes of the "aggregates" when compared to the method above) can be controlled easily. Being able to create other shapes could result in new arrangements to form the tissue-engineered meat.

In addition to facilitating scalability and therefore sustainability of the meat production, introducing a pectin-based microcarrier phase into the engineered meat may impart an additional level of control over the desirable food properties such as nutritional value and palatability. For example, the microcarriers can be composed of material with health benefit not usually provided by meat, such as pectin. Pectin is known for its positive effect as a fiber and as an anti-inflammatory agent. Further, a hydrogel microcarrier phase can add moisture content to improve the mouthful feeling (usually linked to the fat content of meat) of the engineered meat. Moisture content can be easily controlled by varying cell/microcarrier ratios through microcarrier size and porosity.

Finally, Hydrogel particles have a long history of use as depots for targeted molecule delivery. Introducing a hydrogel microcarrier core to engineered meat provides a depot to encapsulate molecules for cellular growth and differentiation during the production process, as well as improve visual and nutritional content of the final engineered meat product.

Thus, the methods of fabricating fully edible microcarriers, and particularly those composed of pectin and cardosin, may result in microcarriers which contain no animal-derived components such as gelatin. These microcarriers may be ideally suited for the fabrication of engineered meat by the method disclosed in Modern Meadow's allowed meat patent. This approach has several advantages over previously described methods which required a multi-step preparation including separate cell expansion and formation of aggregates. A single step is used instead to form fully cellularized microcarriers, which saves time and labor, eliminates the need for cell detachment agents, and provides additional control over the final engineered meat properties such as texture, nutritional value and taste.

For engineered meats, instead of aggregates composed of only cells, this engineered meats described herein provide aggregates of cellularized microcarriers composed of the edible microcarriers that contain cells relevant for the tissue engineering of meat (smooth muscle cells, satellite cells, adipocytes, etc.). As cells reside on the surface of the microcarriers (and may also reside inside, if the microcarriers are porous), contiguously deposited aggregates would fuse the same way they do when the aggregates are composed solely of cells. As these cell-containing microcarrier aggregates are formed in the course of cell expansion, their production is optimized, the process is efficient and economically advantageous.

These edible microcarriers can be formed and/or combined with other molecules/substances with high nutritional value or providing improved texture or adding flavor to the final product. They can also be used for the simultaneous culturing of several cell types with relevance to meat, thus allowing for the engineering of novel foods. For example bovine and fish cells could be cultured simultaneously.

Examples

Figure 6A:
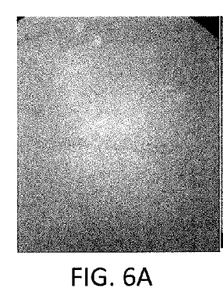
FIGS. 6A-6D illustrate a time course of cellularization of an irregularly-shaped edible, animal-product-free microcarrier as described herein.
Figure 6B:
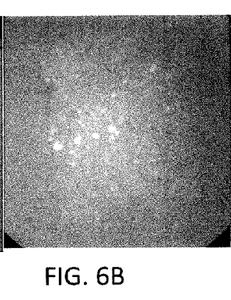
Figure 6C:
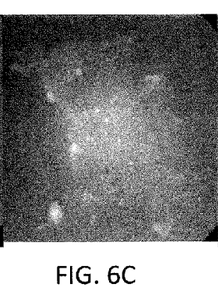
Figure 6D:
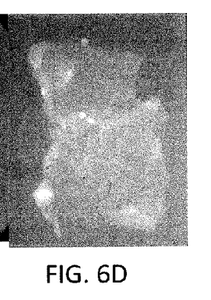
Figure 7A:
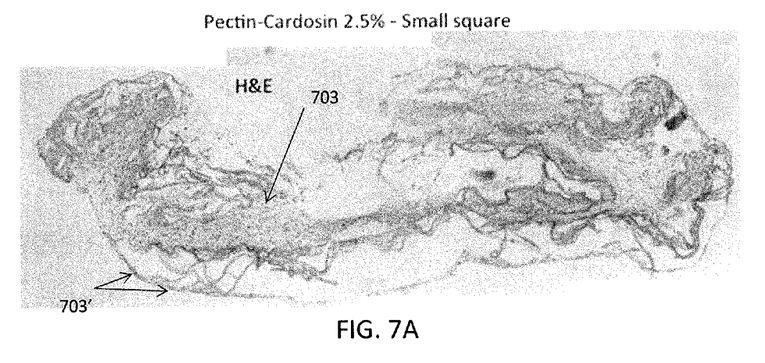
FIGS. 7A and 7B are histological sections through a pectin/RGD-containing polypeptide hydrogel (in this example, pectin-cys 0.75% (w/v) and cardosin 2.5% (w/w)) that has been sectioned.
Figure 7B:
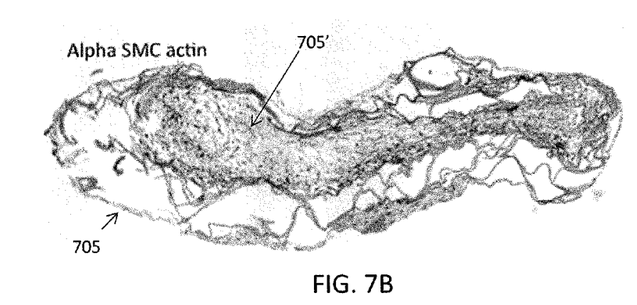

FIGS. 6A-6D show one example of muscle cells cellularizing an edible and animal-product-free microcarrier. In FIG. 6A, muscle cells (smooth muscle cells in this example) were seeded on top of an edible microcarrier composed of pectin-cys 0.75% (w/v) and cardosin 2.5% (w/w). The white 'clumps' on in the figure are clusters of cells seeded onto the hydrogel. As the cells attached to the microcarrier and divided, they also invaded the hydrogel of the microcarrier, causing it to become more opaque, as shown in progressive images 6B, 6C and 6D (showing a time course with a few hours between each image: day 1, 5, 12 and 18, with seeding occurring at day 1). In general, attachment and expansion of cells on/to a microcarrier can be carried on under static conditions, for example in well plates as shown in FIGS. 6A-6D, or in suspension in a bioreactor. When grown in a bioreactor, the cells may be mixed with the suspension of edible microcarriers and the speed of rotation/agitation within the bioreactor may be adjusted over time to ease attachment, for example, including static phases or low speed periods alternating with higher speed periods. In FIGS. 6A-6D, the edible microcarrier hydrogel is irregularly shaped, and the shape becomes more clear as the muscle cells spread over and within the hydrogel. The microcarrier shown in between 1 and 2 mm in diameter. As cell growth proceeds, the cells may continue to grow and fuse on and in the microcarrier further cellularizing the microcarrier. As mentioned above, the term "microcarrier" and "microsponge" may be used interchangeable. In general, a microsponge may be made of the same hydrogel material but may have a different size and/or shape.

Although any of the microcarriers described herein may be porous, as illustrated in FIGS. 6A-7B, pores are not necessary for the cells to invade and grow into the microcarrier (although they may speed this up). For example, histology on a cellularized microcarrier made from pectin-cys and cardosin (such as the example edible microcarrier of FIGS. 6A-6D, above) indicates that the microcarriers may be filled with cells that have inserted into the microcarrier. For example, FIG. 7A shows a section through a microcarrier made of pectin-cys 0.75% (w/v) and cardosin 2.5% (w/w) that has been cellularized (e.g., for greater than 2 hours). The section in FIG. 7A shows an irregularly-shaped microcarrier stained with H&E and shows small muscle cell nuclei 703 within the volume of the microcarrier as well as distributed around the microcarrier 703'. This is confirmed in FIG. 7B, which shows a similar section of an edible microcarrier that has been stained for alpha smooth muscle cell actin, showing actin (and thus smooth muscle cells) surrounding the microcarrier 705 and within the body of the hydrogel microcarrier 705'.

Figure 8A:
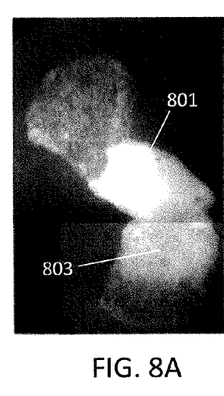
FIGS. 8A-8D illustrate a time course of fusion of two irregularly-shaped cellularized hydrogel microcarriers (edible, animal-product-free microcarriers) that have been placed next to each other (FIG. 8A) and allowed a few hours to progressively fuse by the action of the muscle cells on the outside of the microcarrier (FIGS. 8B, 8D and 8C). The images may be approximately 8 hrs. apart in time. Not that partial fusion occurs very quickly (e.g., within the first few hours).
Figure 8B:
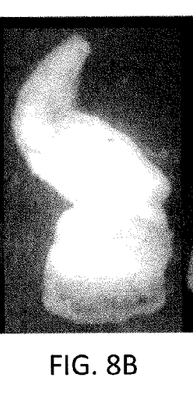
Figure 8C:
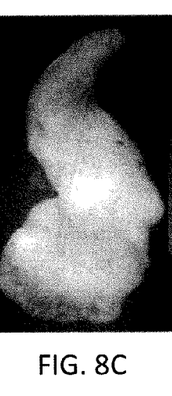
Figure 8D:
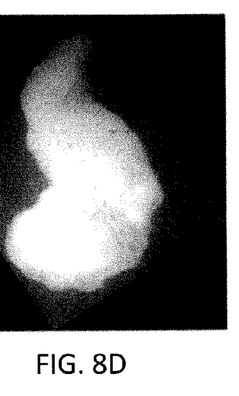

As mentioned, aggregates of cellularized microcarriers may be fused by placing them near (e.g., in some variations immediately adjacent each other and in contact with each other) and allowing the cells on the surface of the microcarrier to fuse. This is illustrated in FIGS. 8A-8D and 9A-9C. FIGS. 8A-8D shows an example of irregularly shaped microcarriers 801, 803 that have been placed adjacent to each other and allowed to fuse. In FIG. 8A, at least the two extreme portions of the microcarriers are incompletely cellularized, but the cellularization continues as they are cultured next to each other. After even a few hours the microcarriers begin to fuse, which continues with longer growth/fusing time, as shown progressively in FIGS. 8B, 8C and 8D (FIG. 8A shows day 1, when the microcarriers are placed in contact; FIG. 9B is day 3; FIG. 8C is day 4, and FIG. 8D is day 11). In this example, the microcarriers may be between 0.1 mm and 2 mm in diameter, and are seeded with smooth muscle cells, grown in culture (e.g., in a dish) and the microcarriers are formed of pectin-cys 0.75% (w/v) and cardosin 2.5% (w/w). The initially incompletely cellularized (uncellularized) portion in the upper right of FIG. 8A has folded back on itself in FIGS. 8B-8D. The 0.75% weight/volume and 2.5% weight/weight referred to above correspond, respectively, to the concentration of pectin in solution and cardosin, but the latter is in relation to pectin. That is, the weight of cardosin in the construct is 2.5% of the weight of pectin in these examples.

Figure 9A:
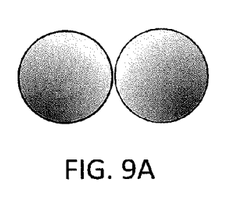
FIGS. 9A-9C schematically illustrate the fusion of cellularized edible, animal-product-free microcarriers.
Figure 9B:
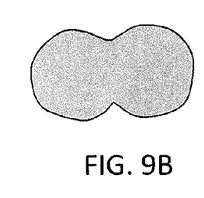
Figure 9C:
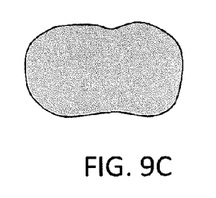

FIGS. 9A-9C illustrate this schematically with spherical microcarriers. The edible, animal-product-free microcarriers are cellularized and placed in contact with each other and allowed to fuse with each other; the muscle cells may continue to expand and invade the hydrogel of the microcarriers. In this manner, aggregates of the cellularized microcarriers may fuse. The time required to fuse is typically faster than that needed to fuse cellular aggregates that do not include microcarriers (taking less than about 80% the time). In FIGS. 9A-9C, the total elapsed time is approximately 24 hours.

Figure 10A:
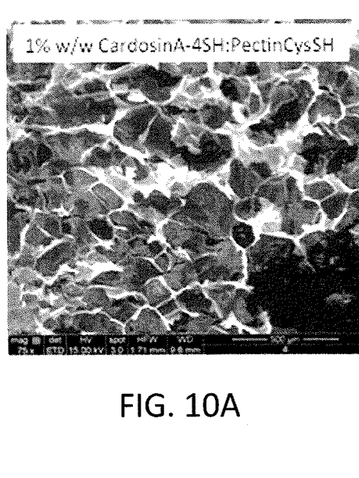
FIGS. 10A-10C show scanning electron microscope (SEM) images of three variations of edible microcarriers formed of pectin (PectinCysSH) and an RGD-containing polypeptide (cardosin A 4-SH), forming hydrogel "sponges" (microsponges or microcarriers) that are 0.75% w/v gels.
Figure 10B:
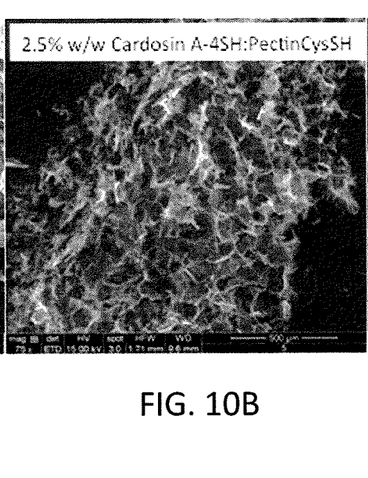
Figure 10C:
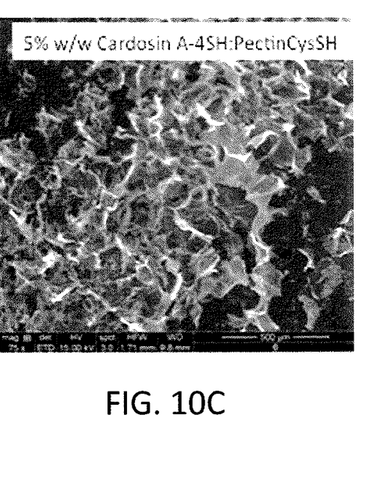

FIGS. 10A-10C show SEMs of dry samples of 0.75% w/v gels forming microcarriers (microsponges) of PectinCySSH and Cardosin A 4-SH at various w/w percentages of cardosin. As shown in FIGS. 10A-10C, the pore size of the resulting material appears to decrease as the percent of cardosin increases, forming less "open" structures with higher percentages of cardosin. 2.5% w/w cardosin was used (as illustrated above) to provide attachment and insertion of muscle cells in culture. The images in FIGS. 10A-10C are in the 500 mm scale range.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skilled in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of forming an edible and animal-product-free microcarrier for use as part of an engineered meat product, the method comprising:
   cross-linking a pectin and an RGD-containing polypeptide to form a pectin/RGD-containing polypeptide hydrogel, wherein cross-linking the pectin and the RGD-containing polypeptide to form the pectin/RGD-containing polypeptide hydrogel comprises cross-linking pectin-thiopropionylamide (PTP) and cardosin; and forming microbeads from the pectin/RGD-containing polypeptide hydrogel having a diameter of between about 0.05 mm and about 3 mm.

2. The method of claim 1, further comprising lyophilizing the pectin/RGD-containing polypeptide hydrogel.

3. The method of claim 1, further comprising: creating the pectin-thiopropionylamide (PTP) by derivatization of pectin with cystamine.

4. A method of forming an edible and animal-product-free microcarrier for use as part of an engineered meat product, the method comprising:

cross-linking a pectin and an RGD-containing polypeptide to form a pectin/RGD-containing polypeptide hydrogel;

thiolating a cardosin polypeptide, wherein cross-linking the pectin and the RGD-containing polypeptide comprises cross-linking the pectin with the thiolated cardosin polypeptide; and forming microbeads from the pectin/RGD-containing polypeptide hydrogel having a diameter of between about 0.05 mm and about 3 mm.

5. The method of claim 1, wherein forming microbeads comprises forming porous microbeads.

6. The method of claim 1, wherein forming microbeads comprises forming microbeads having a diameter of between about 1 mm and about 0.1 mm.

7. A method of forming an edible and animal-product-free microcarrier for use in forming an engineered meat product, the method comprising:

creating pectin-thiopropionylamide (PTP) by derivatization of pectin with cystamine;

thiolating a cardosin polypeptide;

cross-linking the PTP and thiolated cardosin to form a hydrogel;

lyophilizing the hydrogel of cross-linked PTP and cardosin; and forming microbeads from the cross-linked PTP and cardosin.

8. The method of claim 7, further comprising adding one or more of: a flavoring, a flavor enhancer, a colorant, a color enhancer, and a nutritional enhancer.

9. An edible microcarrier that is free of animal products and that is configured for culturing muscle cells to form an engineered meat product, the edible microcarrier having a body comprising a hydrogel of cross-linked pectin and an RGD-containing polypeptide, wherein the body is between about 3 mm and about 0.05 mm in diameter, wherein the pectin comprises thiol-modified pectin (PTP).

10. An edible microcarrier that is free of animal products and that is configured for culturing muscle cells to form an engineered meat product, the edible microcarrier having a body comprising a hydrogel of cross-linked pectin and an RGD-containing polypeptide, wherein the body is between about 3 mm and about 0.05 mm in diameter, wherein the RGD-containing polypeptide comprises a cardosin.

11. The edible microcarrier of claim 9, wherein the body has a diameter of between about 2 mm and about 0.05 mm in diameter.

12. The edible microcarrier of claim 9, wherein the body has a diameter of between about 1 mm and about 0.1 mm in diameter.

13. The edible microcarrier of claim 9, wherein the body is porous.

14. The edible microcarrier of claim 9, further comprising an additive consisting of one or more of: a flavoring, a flavor enhancer, a colorant, a color enhancer, and a nutritional enhancer.

15. An edible microcarrier that is free of animal products and that is configured for culturing muscle cells to form an engineered meat product, the edible microcarrier having a body comprising a hydrogel of thiol-modified pectin and cardosin, wherein the body is between about 3 mm and about 0.05 mm in diameter.

* * * * *